United States Patent [19]

Shiokawa et al.

[11] Patent Number: 4,600,792
[45] Date of Patent: Jul. 15, 1986

[54] PREPARATION OF BIPHENYLYLSULFONYLUREAS AND INTERMEDIATES THEREFOR

[75] Inventors: Kozo Shiokawa, Kanagawa; Shinzo Kagabu; Koichi Moriya, both of Tokyo, all of Japan

[73] Assignee: Nihon Tokushu Noyaku Seizo K.K., Tokyo, Japan

[21] Appl. No.: 720,826

[22] Filed: Apr. 8, 1985

[30] Foreign Application Priority Data

Apr. 11, 1984 [JP] Japan .................. 59-70909

[51] Int. Cl.⁴ .............................. C07C 143/83
[52] U.S. Cl. ..................... 560/12; 544/211; 544/320; 544/332; 71/88
[58] Field of Search ........................... 560/12

[56] References Cited

U.S. PATENT DOCUMENTS

| | | | |
|---|---|---|---|
| 3,649,674 | 3/1972 | Hoyer | 560/159 |
| 3,933,894 | 1/1976 | Stephens | 560/12 |
| 4,097,676 | 6/1978 | Romano | 560/137 |
| 4,230,874 | 10/1978 | Pallos | 560/12 |

FOREIGN PATENT DOCUMENTS 557074 10/1957 Belgium .................. 560/12

*Primary Examiner*—Michael L. Shippen
*Attorney, Agent, or Firm*—Sprung, Horn, Kramer & Woods

[57] ABSTRACT

The novel process

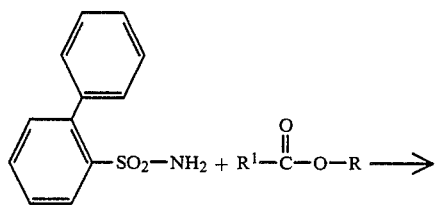

(v)  (iv)

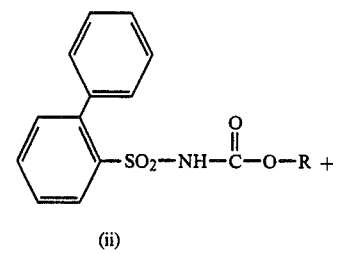

(ii)

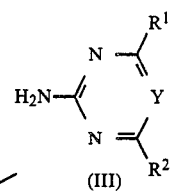

(III)

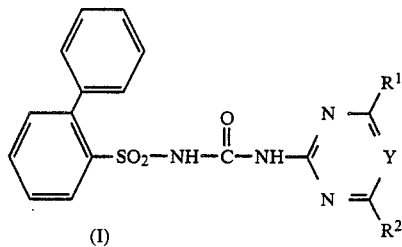

(I)

in which
R is a lower alkyl group or an aryl group
R¹ is a chlorine atom or —O—R, and
Y is CH or N.

The end products I are known herbicides. Intermediates (II) are new.

1 Claim, No Drawings

PREPARATION OF BIPHENYLYLSULFONYLUREAS AND INTERMEDIATES THEREFOR

DETAILED DESCRIPTION OF THE INVENTION

This invention relates to a process for biphenylylsulfonylurea derivatives, intermediates thereof, and a process for producing the intermediates.

More specifically, this invention relates to a process for producing biphenylylsulfonylurea derivatives represented by the following formula (I)

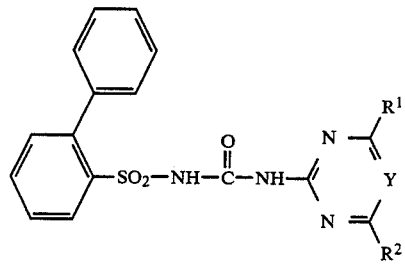

wherein each of $R^1$ and $R^2$ represents a lower alkyl group or a lower alkoxy group, and Y represents CH or N, which comprises reacting a biphenylylsulfonylcarbamate derivative represented by the following formula (II)

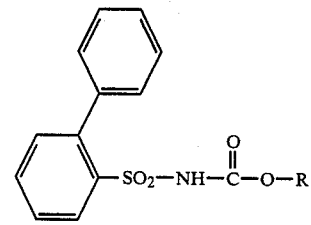

wherein R represents a lower alkyl group or an aryl group, with a compound represented by the following formula (III)

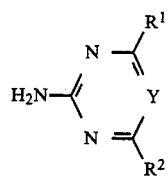

wherein $R^1$, $R^2$ and Y are as defined above.

The biphenylylsulfonylcarbamate derivative of general formula (II) is a novel compound which can be synthesized by reacting 2-phenylbenzenesulfonamide represented by the following formula (v)

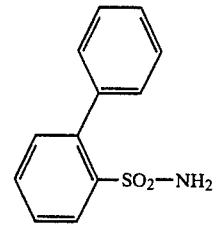

with a compound represented by the following formula (IV)

wherein R is as defined above, and R' represents a chlorine atom or the group —O—R in which R is as defined above.

The present inventors made investigations on a new process for producing the biphenylsulfonylurea derivatives having excellent selective herbicidal activity which are disclosed in the specification of Japanese Laid-Open Patent Publication No. 123,168/1982, and have now found that the compounds of formula (I) can be easily produced in high purities and yields by a different process from the process disclosed in the above known publication, namely by reacting the biphenylylsulfonylcarbamate derivative of formula (II) with the compound of formula (III) above.

In this new process, the biphenylylsulfonylcarbamate derivative of formula (II) used as an intermediate is a novel compound not described in publications known before the filing date of the present application and is industrially useful as an intermediate for the synthesis of the useful compounds of formula (I) and also as an intermediate for other syntheses. It has been found that this intermediate can be easily produced by reacting 2-phenylbenzenesulfonamide of formula (V) with the compound of formula (IV), as stated hereinabove.

In the process for producing a biphenylylsulfonylurea derivative described in the specification of the above-cited Japanese Laid-Open Patent Publication No. 123,168/1982, sulfonyl isocyanate is used as an intermediate. The production of the sulfonyl isocyanate, however, has the industrial disadvantage that there is used phosgene or its derivative, trichloromethyl chloroformate, which has a toxicity problem and is disadvantageous in handling. Furthermore, to obtain good results, the reaction temperature should be considerably high, for example 120° to 130° C. Another disadvantage is that in order to obtain the desired sulfonyl isocyanate by performing the reaction efficiently, the use of a catalyst such as 1,4-diazabicyclo[2,2,2]octane is necessary.

The investigations of the present inventors have led to the discovery that there can be provided excellent processes suitable for industrial practice by which the aforesaid disadvantages of the prior art can be overcome, the novel compound of formula (II) can be produced easily and quantitatively by one-step reaction at room temperature from the compound of formula (V) and the compound of formula (IV), and by the reaction of the compound of formula (II) with the compound of formula (III), the biphenylylsulfonylurea derivative of formula (I) can be produced easily and safely in a high purity and yield.

It has also been found that the biphenylylsulfonylcarbamate derivative of formula (II) in accordance with this invention is a novel compound which is not only useful industrially as an intermediate for the production of the compound of formula (I) and as an intermediate for other syntheses, but also has by itself a certain kind of physiological activity (e.g., agricultural chemicals).

It is an object of this invention therefore to provide a new process for producing the biphenylylsulfonylurea derivatives of formula (I), the biphenylylsulfonylcarbamate derivative of formula (II) as its intermediate, and a process for producing the carbamate derivative.

The above and other objects and advantages will become more apparent from the following description.

The process for producing the biphenylylsulfonylurea derivatives of this invention can be shown by the following reaction scheme:

Process (i)

$$\text{biphenyl-SO}_2\text{-NH-C(O)-O-R} + \text{H}_2\text{N}-\underset{R^2}{\overset{R^1}{\underset{N=}{\overset{N-}{\bigg\langle}}}}Y \longrightarrow$$

(II)    (III)

$$\text{biphenyl-SO}_2\text{-NH-C(O)-NH}-\underset{R^2}{\overset{R^1}{\underset{N=}{\overset{N-}{\bigg\langle}}}}Y$$

(I)

In the formulae, R, $R^1$, $R^2$ and Y are as defined hereinabove.

In the above reaction scheme, R in the compound of formula (II) represents a lower alkyl group or an aryl group. Specific examples are lower alkyl groups such as methyl, ethyl, propyl, isopropyl, and n-(iso-, sec-, or tert-)butyl, and aryl groups such as phenyl, naphthyl, methylphenyl and chlorophenyl.

In the above reaction scheme, $R^1$ and $R^2$ in the compounds of formulae (III) and (I) each represent a lower alkyl or alkoxy group. Specifically, there may be cited the same lower alkyl groups as exemplified above, and lower alkoxy groups having the same lower alkyl groups as exemplified above.

Specific examples of the biphenylylsulfonylcarbamate derivative of general formula (II) as a starting material include phenyl 2-biphenylylsulfonylcarbamate, methyl 2-biphenylylsulfonylcarbamate, ethyl 2-biphenylsulfonylcarbamate, 2-tolyl 2-biphenylylsulfonylcarbamate, 4-tolyl 2-biphenylylsulfonylcarbamate, α-naphthyl 2-biphenylylsulfonylcarbamate and 4-chlorophenyl 2-biphenylylsulfonylcarbamate.

Specific examples of the compound of general formula (III), which is likewise a starting material, include 2-amino-4,6-dimethoxy-1,3,5-triazine, 2-amino-4,6-dimethyl-1,3,5-triazine, 2-amino-4-methoxy-6-methyl-1,3,5-triazine, 2-amino-4,6-dimethylpyrimidine, 2-amino-4-methoxy-6-methylpyrimidine, and 2-amino-4,6-dimethoxypyrimidine.

By citing the following typical example, the above process of this invention will be specifically described:

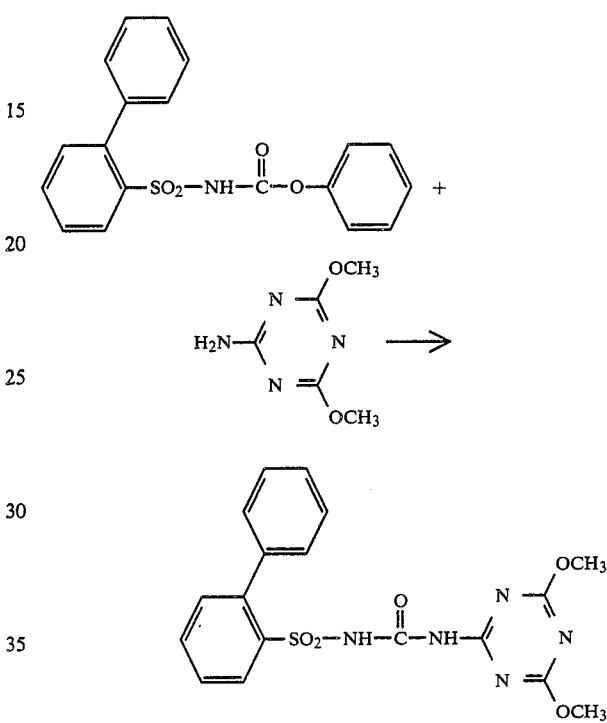

Desirably, the above process of the invention is carried out by using a solvent or diluent. For this purpose, all inert solvents and diluents can be used.

Examples of such solvents or diluents include aliphatic, alicyclic and aromatic hydrocarbons (which may optionally be chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, di-isopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; alcohols such as methanol, ethanol, isopropanol, butanol and ethylene glycol; esters such as ethyl acetate and amyl acetate; acid amides such as dimethylformamide and dimethylacetamide; sulfones and sulfoxides such as dimethyl sulfoxide and sulfolane; and bases such as pyridine.

The above reaction can be carried out in the presence of an acid binder. Illustrative of such an acid binder are the hydroxides, carbonates, bicarbonates and alcoholates of alkali metals, and tertiary amines such as triethylamine, diethylaniline and pyridine, which are generally used.

The above process can be carried out over a broad temperature range. For example, it can be carried out at a temperature between about −20° C. to the boiling point of the mixture, preferably between 0° and about 100° C. Desirably, the reaction is carried out under atmospheric pressure, but it is also possible to operate under elevated or reduced pressures.

The biphenylylsulfonylcarbamate derivative of general formula (II) in accordance with this invention may be produced by the following process:

Process (ii)

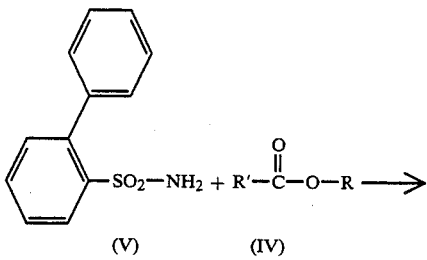

(V)        (IV)

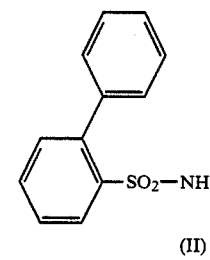

(II)

In the above formulae, R and R' are as defined above.

In the above reaction scheme, examples of R may be the same as those given hereinabove with regard to the process (i). R' represents a chlorine atom or the group —O—R in which R is as defined above.

In the process for producing the biphenylylsulfonylcarbamate derivative of general formula (II) in accordance with this invention by the above reaction scheme, specific examples of the compound of general formula (IV) as a starting material include diphenyl carbonate, methyl chloroformate, ethyl chloroformate, phenyl chloroformate, dimethyl carbonate, diethyl carbonate, di(α-naphthyl)carbonate, di-2-tolyl carbonate, di-4-tolyl carbonate and bis-(4-chlorophenyl)carbonate.

By citing the following typical example, the process for producing the compound of formula (II) will be specifically described:

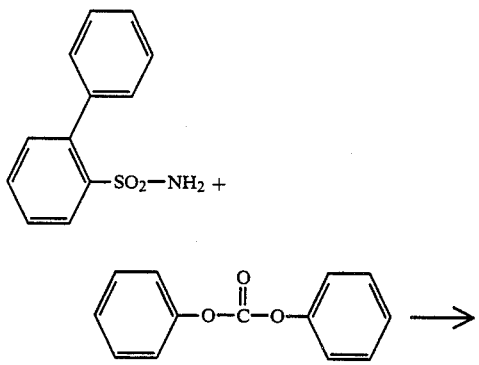

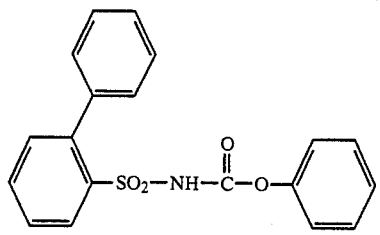

To carry out the above process, the same inert solvent or diluent as exemplified above is desirably used, and the desired compound can be used in a high purity and a high yield.

The above process can be carried out over a broad temperature range, generally at a temperature between −20° C. and the boiling point of the mixture, preferably between 0° and about 100° C. Desirably, the reaction is carried out under atmospheric pressure, but it is also possible to operate under elevated or reduced pressure.

The following examples illustrate the present invention more specifically. It should be understood however that the invention is not limited to these examples alone.

EXAMPLE 1

Synthesis of the compound of this invention represented by general formula (II):

Sodium hydride (2.6 g) was added to dry dimethylformamide (200 ml), and at less than 10° C., a solution of 2-phenylbenzenesulfonamide (23.3 g) in dimethylformamide (50 ml) was added. The mixture was then stirred at room temperature for 1 hour, and diphenyl carbonate (21.4 g) was added at room temperature. The mixture was further stirred at room temperature for 1 hour. Then, after the whole mixture was added to ice water, the mixture was acidified with hydrochloric acid and extracted with ethyl acetate. The organic layer was dehydrated, and ethyl acetate was distilled off under reduced pressure to give phenyl N-(2-biphenylylsulfonyl)carbamate (35 g) as a solidified desired compound represented by the following formula. mp. 114°–117° C.

(Compound No. 1)

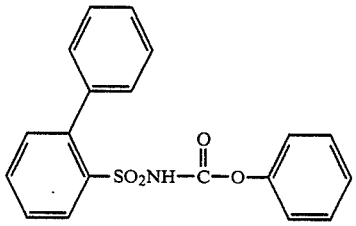

By the same method as in Example 1, the materials shown in the following table were reacted to form the compounds of general formula (II) in accordance with this invention, which are shown in Table 1 below.

TABLE 1

| Starting material | Starting material | Product (compound No.) |
| --- | --- | --- |
| 2-Phenylbenzene-sulfonamide | Methyl chloroformate | Methyl N—(2-biphenylylsulfonyl)carbamate, m.p. 156–158° C. (No. 2) |
| 2-Phenylbenzene-sulfonamide | Di-α-naphthyl carbonate | α-Naphthyl N—(2-biphenylylsulfonyl)-carbamate (No. 3) |

TABLE 1-continued

| Starting material | Starting material | Product (compound No.) |
|---|---|---|
| 2-Phenylbenzene-sulfonamide | Di-2-tolyl carbonate | 2-Tolyl N—(2-biphenylyl-sulfonyl)carbamate (No. 4) |
| 2-Phenylbenzene-sulfonamide | bis-(4-Chlorophenyl) carbonate | 4-Chlorophenyl N—(2-biphenylylsulfonyl)car-bamate (No. 5) |
| 2-Phenylbenzene-sulfonamide | Diethyl carbonate | Ethyl N—(2-biphenylyl-sulfonyl)carbamate, m.p. 147–150° C. (No. 6) |

Below is shown an example of synthesis of the compound of general formula (I) using phenyl N-(2-biphenylylsulfonyl)carbamate synthesized according to the method shown in Example 1.

EXAMPLE 2

Phenyl N-(2-biphenylylsulfonyl)carbamate (35.3 g) and 2-amino-4,6-dimethoxy-1,3,5-triazine (15.6 g) were added to dioxane (200 ml), and the mixture was refluxed with stirring for 2 hours. The reaction mixture was cooled to room temperature and the precipitated crystals were collected by filtration. The crystals were washed with diethyl ether and dried to give the desired 1-(2-biphenylylsulfonyl)3-(4,6-dimethoxytriazin-2-yl)urea (36 g) represented by the following formula. m.p. 175°–180° C.

(Compound A)

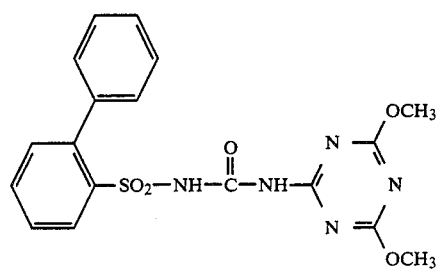

The biological effect of the compound A synthesized in Example 2 is illustrated in the following Example 3.

EXAMPLE 3

Wagner pots (1/5,000 are) were filled with paddy soil, and rice seedlings in the 2- to 3-leaf stage (height about 10 cm), two per pot, were transplanted. Seeds of barnyard grass (*Panicum crus-galli*), flat sedge (*Cyperus microiria*), monochoria (*Monochoria vaginalis*), bulrush (*Scirpus juncoides*) and broad-leaved weeds, small pieces of spikerush (*Eleocharis acicularis*), and tubers of mizu-gayatsuri (*Cyperus serotinus*) and urikawa (*Sagitaria pygmaea*) were inoculated in the pots, and the soil in the pots was maintained in the wet state. When the barnyard grass grew to about a two-leaf stage (about 7 to 9 days after inoculation), the pots were watered to a depth of about 6 cm, and compound A in the form of an emulsion was applied to each of the pots in a predetermined amount by means of a pipette. After this treatment, the water was allowed to leak from the pots at a rate of 2 to 3 cm per day, and thereafter each of the pots was maintained in the watered state to a depth of about 3 cm. In the fourth week after the treatment with the chemical, the herbicidal effect and the degree of phytotoxicity were evaluated. It was found that the compound A showed a herbicidal effect of 100% on each of the weeds when applied in an amount of 0.2 kg/ha (the amount of the active component), and no phytotoxicity on rice was observed.

It will be understood that the specification and examples are illustrative but not limitative of the present invention and that other embodiments within the spirit and scope of the invention will suggest themselves to those skilled in the art.

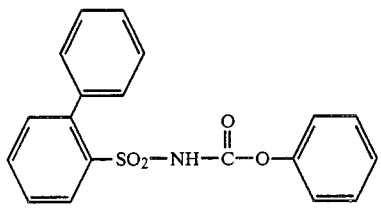

We claim:

1. Phenyl 2-biphenylylsulfonylcarbamate of the formula